United States Patent [19]

Ahlquist

[11] Patent Number: 4,885,248
[45] Date of Patent: Dec. 5, 1989

[54] TRANSFER VECTOR

[75] Inventor: Paul G. Ahlquist, Madison, Wis.

[73] Assignee: Lubrizol Genetics, Inc., Wickliffe, Ohio

[21] Appl. No.: 12,739

[22] Filed: Mar. 9, 1987

Related U.S. Application Data

[63] Continuation-in-part of Ser. No. 580,445, Feb. 14, 1984, abandoned.

[51] Int. Cl.$^4$ ............... C12N 15/00; C12R 1/41; C12R 1/185; C07H 15/12
[52] U.S. Cl. ............... 435/172.3; 435/252.3; 435/252.33; 435/320; 536/27; 935/31; 935/39; 935/72; 935/73
[58] Field of Search ............... 435/172.3, 253, 320, 435/252.3, 252.33; 536/27

[56] References Cited

PUBLICATIONS

Roberts et al., 1979, Proc. Natl. Acad. Sci., 76(11): 5596–5600.
Queen, C., 1983, J. Mol. Appl. Genet. 2:1–10.
Old and Primrose, "Principles of Gene Manipulation", Third Edition, Blackwell Scientific Publications, Oxford, UK, pp. 99–101.
Soberon et al., (1982), Promoters: Structure and Function, in Rodriguez et al., (eds.), Praeger Publishers, New York, N.Y., p. 407.
Pouwels et al., (1985), in Cloning Vectors: A Laboratory Manual, Elsevier, Amsterdam, The Netherlands, p. 1–B–iv–4.
Kessler et al., (1986), Gene 47: 1–153.
Tabor and Richardson, (1985), Proc. Natl. Acad. Sci., U.S.A., 82:1074.
Ahlquist and Janda, (1984), Mol. Cell Biol. 4:2876.
O'Rear et al., (1980), Cell 20:423.
Dunn et al., (1983), J. Mol. Biol. 166:477–535.
Davanloo et al., (1984), Proc. Natl. Acad. Sci., U.S.A., 81:1074.

Primary Examiner—Charles F. Warren
Assistant Examiner—David T. Fox
Attorney, Agent, or Firm—Greenlee and Associates

[57] ABSTRACT

A recombinant DNA vector is provided as a universal transcription vector having a replication origin and selectable marker, a promoter and a transcription initiation site comprising a first transcribed nucleotide, wherein a restriction site is provided immediately adjacent to and upstream from the transcription initiation site so as to separate transcribed from untranscribed nucleotides. A second restriction site may also be positioned downstream from the said restriction site. Precise control of initiation and termination of transcription is attained by this invention. Such control is important in assuring the effectiveness of transcribed RNA viral vectors.

A high fidelity in vitro RNA transcription method is also provided utilizing vectors constructed from the universal transcription vector, or other vectors producing transcripts having no more than one extra 5' base. This method is capable of producing functional RNA transcripts, preferably comprising infectious viral sequences.

24 Claims, 5 Drawing Sheets a. Pr promoter/polylinker fusion in pPR1
   (a progenitor of pB3PR13)

b. Pm promoter/polylinker fusion in pPM1

(FROM C. QUEEN (1983) J. MOL APPL. GENET. 2:1-10)

Map of EcoRI - linearized pB3PR13

TRANSFER VECTOR

CROSS-REFERENCE TO RELATED APPLICATIONS

This application is a continuation-in-part of application Ser. No. 580,445, filed Feb. 14, 1984, now abandoned.

FIELD OF THE INVENTION

This invention relates to the field of recombinant DNA and RNA vectors and processes for making and using same, particularly for the production of infectious viral RNA.

BACKGROUND OF THE INVENTION

The nucleotide sequences of a DNA molecule carry an information code which can be transcribed into an intermediate messenger (mRNA) followed by translation into a protein. Such a protein may have a catalytic or a structural function in the organism. In some cases the nucleotide sequence is transcribed into an RNA molecule and this RNA molecule is the functional entity. Natural examples are the ribosomal RNA molecules (rRNA), transfer RNA molecules (tRNA) and small nuclear RNA molecules (snRNA). Some viruses (e.g., retroviruses) are reverse transcribed and the DNA product is then incorporated into the host genome from whence it can be transcribed once again into viral RNA. A useful artificial situation would be to isolate a DNA fragment of exactly the same sequence as a useful RNA molecule and then to insert such a fragment precisely at the transcription initiation site downstream from a strong promoter sequence which in turn has been inserted into a vector plasmid. In such a case large quantities of the desired RNA molecule could be produced by in vitro transcription. Prior vector systems have provided insertion sites downstream from a promoter, but the RNA transcribed therefrom contains extraneous sequence at the 5' end. The function of the resulting RNA may be modified in an undesired or uncontrolled manner since many RNA functions are affected by the nucleotide sequence at the 5' end. This prior art difficulty could be overcome by a transcription vector providing for precise initiation of transcription of the inserted DNA segment. In this manner it is possible to produce wild type viral RNA sequences, mutated viral RNA sequences, viral RNA sequences in which some nonessential nucleotide sequences have been replaced by useful foreign genes and wild type or mutated rRNA, tRNA or sRNA molecules. Mutated viral RNA sequences may be used to infect plant cells thereby preventing superinfection or viral RNA sequences partly replaced by foreign genes may be used as vehicles for the introduction of those genes into plant cells. Alternatively the metabolism of microbial populations may be disrupted by transformation of the population with the recombinant plasmid carrying mutated rRNA, tRNA or snRNA.

In the past several years a very large potential has developed in the field of genetic engineering for the transfer of foreign genes to plants. In order to achieve such a transfer, it is necessary to find suitable vectors. The most advanced work on transfer of genes to a plant genome has been achieved by the use of *Agrobacterium tumefaciens* and, to a lesser extent, *Agrobacterium rhizogenes* (Leemans, J., et al. (1982) in Kahl, G. and J. S. Schell (1982) Molecular Biology of Plant Tumors Ch. 21:537–545, Academic Press, New York). A recent study (Murai, N., et al. (1983) Science 222:476–482) showed that sequences coding for the bean seed protein phaseolin were inserted into the sunflower genome by the transferred DNA regions of tumor inducing plasmids. In one instance the phaseolin encoding sequences were controlled by the octopine synthase promoter and in another instance by the phaseolin promoter region. In both cases the phaseolin genes were correctly transcribed, processed and translated, thus demonstrating the expression of a plant gene after transfer to a taxonomically distinct botanical family.

In addition, there is the potential of genetically engineering the normal plasmids of Rhizobium strains prior to the infection and formation of nodules on plant roots. Much work has already been done on the structure and function of nitrogenase genes (Scott, K. F., Rolfe, B. G. and J. Shine (1983) DNA 2:141–148; Scott, K. F., Rolfe, B. G. and J. Shine (1983) DNA 2:149–156). The promoter of the nitrogenase genes of these organisms have been used to control the transcription and translation of a variety of foreign genes inserted into the symbiotic plasmids of Rhizobium in such a manner as to be under the control of these promoter regions (EPO Publication No. 0,130,047, published Jan. 2, 1985). Both types of vectors, i.e., the T-DNA of Agrobacterium spp. and the symbiotic plasmids of Rhizobium spp., involve the transfer of foreign genes as DNA.

Another possibility for the transfer of foreign genes to plant cells is by the use of RNA or DNA viruses. For retroviruses, which replicate their RNA through DNA intermediates, naturally occurring infectious viral DNA forms can be isolated (J. O'Rear et al. (1980) Cell 20:423). Other RNA viruses replicate their genomes without passing through a DNA stage. In the case of these viruses, it would be necessary to reverse transcribe them into cDNA molecules because of the technical difficulties of handling RNA molecules and the lack of restriction endonuclease active on RNA. In some cases where amplification by secondary infection cycles is possible, e.g., poliovirus (Racaniello, V. and D. Baltimore (1981) Science 214:916–919) and potato spindle tuber virus (Cress, D., Kiefer, M. and R. A. Owens (1983) Nucleic Acids Res. 11:6821–6835), the method appears feasible, but in many examples, infectivity of viral cDNA molecules is low or nonexistent, and this approach does not produce results. Despite attempts in a number of laboratories, complete genomic cDNA clones from a range of other RNA viruses have not yet proved directly infectious. To understand why these negative results may occur, it is useful to list the following probable requirements for infectivity of directly-inoculated viral cDNA:

(1) cDNA uptake into the cell; (2) cDNA transport into the nucleus; (3) transcription of (at least) full-length viral RNA's (vRNA); (4) avoidance of vRNA splicing; (5) processing of vRNA termini to infectious forms; (6) vRNA transport to the cytoplasm; (7) translation of (at least some) viral proteins; and (8) effective interaction of vRNA with viral and cellular proteins for a first round of replication.

Although effective transcription is often considered to be the most critical feature, viral cDNA infectivity probably involves a number of additional requirements. For example, linkage of viral cDNA to a strong plant promoter might be a useful strategy but would not give infectivity if the viral RNA contains a cryptic splice site which leads to its effective processing to a non-infectious form. Also, a number of steps, e.g. (4) to (6) above, involve cellular processes which are poorly understood. Consequently, the infectivity of directly-inoculated cDNA could be severely limited at a number of steps, e.g., vRNA transport to the cytoplasm. These defects of infectivity would be extremely difficult to identify and so the various defects would be very difficult to correct without significant advances in basic molecular and cellular biology.

Several features are needed to turn a fragment of nucleic acid into a plant vector: (1) The nucleic acid should be capable of being cloned so that useful quantities can be recovered; (2) The nucleic acid should be able to replicate within a plant cell and preferably, should be recognizable by selective methods; (3) It should not be pathogenic; (4) The nucleic acid must be capable of incorporating other nucleic acid sequences into its structure and of expressing such incorporated nucleic acid; and (5) If heritable changes of the transformed plant are wanted, then the vector or a derivative of the vector should be stably maintained from one generation to the next. Further, in the case of T-DNA, at some stage the transformed plant cell will have to be purified by cloning and regenerated into a plant. When these features are considered in relation to RNA plant viruses, a number of difficulties become apparent: (1) The techniques of genetically manipulating and recombining RNA are much more difficult than the techniques of genetically manipulating and recombining DNA; (2) Since most virus particles are packaged into protein capsids, there may be difficulties in accommodating more than limited quantities of "foreign" nucleic acid; (3) RNA viruses need to be replicated within the plant cell so there will be difficulties in recovery of genetically engineered RNA; (4) The strain of RNA viruses used to infect the plant cells should cause minimal pathogenic effects.

The majority of known viruses infecting eukaryotes encapsidate RNA genomes. This is particularly true among plant viruses, where 24 of 28 recognized groups produce particles containing RNA (R. E. F. Matthews (1982) Intervirology 17:1). Cloning and manipulating cDNA copies of such viral RNAs has greatly facilitated progress in RNA virology in recent years. However, use of recombinant DNA technology in the study of most RNA viruses has been seriously limited by inability to express infection from viral cDNA clones. Methods to overcome this limitation by constructing complete viral cDNA clones from which infectious products can be produced by in vitro transcription are needed. Expression of viral cDNA by such methods allows detailed molecular genetic analysis of RNA virus replication, gene expression, and regulation and the construction of practical expression vectors based on RNA viruses.

SUMMARY OF THE INVENTION

A method of constructing a recombinant plasmid carrying a vector, a strong promoter and a restriction endonuclease site at the transcription initiation point is described. This restriction endonuclease site is used to insert the desired DNA fragment.

The techniques of recombinant DNA have made it possible to transcribe and translate a variety of open reading frames in a DNA sequence. The efficiency of such transcription and translation depends on many factors, e.g., the "strength" of the promoter region, the structure of DNA sequences upstream from the transcription intitiation site, and, in some cases, the DNA structure on the 3' side of the termination signal. In some cases it is useful to produce an RNA transcript with precise initiation and termination points, e.g., for the in vitro production of viral RNA molecules, small nuclear RNA molecules and rRNA molecules. This invention describes the production by use of advanced genetic engineering techniques of a recombinant plasmid containing a restriction endonuclease site at a point downstream from a strong promoter, preferably a lambda virus promoter (PR) where transcription from various DNA sequences can be precisely initiated. In addition, a restriction site, preferably an EcoRI site, occurs immediately after the transcription initiation site so the use of the restriction immediately prior to transcription in vitro will also precisely locate the termination point (within 7 nucleotides) of any DNA fragment inserted into the initiation restriction endonuclease site.

A preferred embodiment of the universal transcription vector of this invention is designated pPM1, and was deposited with the American Type Culture Collection Depository in Rockville, Maryland on March 7, 1985, as ATCC No. 40172.

A preferred recombinant DNA vector of this invention comprises: (a) a replication origin and selectable marker; (b) a nucleotide sequence comprising promoter sequences and a transcription initiation site wherein a transcription initiation nucleotide is the first transcribed nucleotide; (c) a restriction endonuclease recognition sequence whose cleavage site is downstream from said promoter on the 3' side of the transcription initiation nucleotide and no more than 1 base removed therefrom.

The promoter sequence often is modified from the natural promoter sequence so as to contain a portion of the restriction endonuclease recognition sequence. Preferably the restriction endonuclease recognition sequence is a blunt-end restriction endonuclease site, most preferably SmaI.

The promoter sequence may be any promoter sequence capable of regulating RNA polymerase. Preferably the promoter sequence is that of pPM1, a $P_R$-lambda phage promoter. Other preferred promoters are the T7$\phi$10 and SP6 promoters, although any promoter known to the art may be used. Such promoters may be synthetically derived, or derived from organelles or nuclear regions of many organisms including bacteria, bacteriophages, viruses, fungi and algae, plants and animals.

Any replication origin and selectable marker known to the art may be used, preferably those of pUC9 or M13mp9.

The vectors of this invention may also comprise inserted sequences coding for desired RNA transcripts inserted at the above-mentioned cleavage site. Preferred RNA sequences are viral RNA sequences, symptomless viral RNA sequences, rRNa, tRNA, and snRNA, or mutated forms of the foregoing.

In a second embodiment of this invention, the vector contains such inserted sequences and lacks a restriction endonuclease site, or part thereof at the junction between the inserted sequence and the promoter sequence; however, the first-transcribed nucleotide must be the first nucleotide of the desired RNA transcript, or must be immediately adjacent and 5' to said first nucleotide of the desired RNA transcript.

The vectors of this invention may also contain an endonuclease recognition sequence on the 3' side of the endonuclease recognition sequence mentioned above, and immediately adjacent thereto. When exogenous DNA to be transcribed is inserted between the two recognition sequences, it is possible to controllably terminate transcription so that the transcript contains no more than seven additional bases on the 3' end.

The vectors of this invention may be prepared by processes known to the art as described in the Examples hereof. A preferable method for preparing a universal transcription vector of this invention comprises the steps of: (a) isolating a DNA fragment containing a promoter; (b) inserting said DNA fragment into the replicative form of a filamentous single-stranded phage strain to produce a recombinant filamentous single-stranded phage; (c) transforming a bacterial strain with said recombinant phage; (d) isolating ssDNA of said recombinant phage excreted from said bacterial strain; (e) synthesizing an oligonucleotide primer partially complementary to said promoter, the 5' end of said oligonucleotide primer corresponding to a transcription initiation site and said 5' end having a sequence complementary to one side of a blunt-end restriction endonuclease site; (f) replicating said ssDNA using said oligonucleotide primer to produce a modified complementary DNA strand containing a modified promoter, the modified promoter being the promoter comprising a sequence complementary to said oligonucleotide primer; (g) replicating said modified complementary DNA strand to produce a modified double stranded DNA fragment containing said modified promoter; and (h) cloning said modified double stranded DNA fragment into a vector plasmid resulting in a universal transcription vector. The term "one side" as used in step (e) above relative to a restriction site means the side of the site containing all the bases on one side of the cut side.

Any DNA fragment containing an appropriate promoter as described above may be used. In one embodiment the fragment is a cI-$P_{RM}$-$P_R$ from phage lambda. Other preferred promoters are T3, T7 ($\phi$10) and SP6. "Promoter" as used herein means sequences having the function of a promoter, i.e., in initiation of transcription. A promoter useful herein need not be the entire sequence of the promoter in its naturally-occurring form, but can merely be sufficient sequences of the naturally occurring promoter to function equivalently to the naturally-occurring promoters. Many means for isolating and constructing such functional promoters not requiring undue experimentation are known to the art and, for example, may involve simply testing the proposed promoter in a vector construct having a reporter gene. Filamentous single stranded phage strains are known to the art, such as M13mp9. Any bacterial strain may be used for transforming with the recombinant phage. Preferred bacterial strains are *E. coli* K12JM101 and 103.

The means for constructing appropriate primers will be apparent to those skilled in the art. The primer used in the preferred embodiment of this invention is 5'-OH-d(GGGACCATTATCACC)-3'-OH, used with the preferred restriction site, a SmaI site. When other restriction sites are used, other primers may be constructed as known to the art.

The process of making the universal transcription vectors of this invention also includes the insertion of DNA fragments corresponding to desired RNA transcripts at the restriction site.

An in vitro process for preparing high-tolerance RNA transcripts is also provided by this invention. The term "high-tolerance" as used herein means transcript having no more than one extra base at the 5' end. It has been found that viral RNA transcripts having one more than one extra base at the 5' end are not efficiently infective to whole plants. Recombinant DNA vectors in which the transcription intitiation nucleotide corresponds to the extreme 5' nucleotide of the desired functional RNA in its natural state are included within the scope of this invention, as are vectors in which the first transcribed nucleotide is immediately adjacent to the nucleotide corresponding to the extreme 5' nucleotide of the desired functional RNA.

Such high tolerance RNA transcripts are prepared in vitro by:
(a) preparing a cDNA sequence corresponding to the RNA transcript desired;
(b) providing a promoter sequence attached to said cDNA sequence capable of controlling transcription thereof in an in vitro environment;
(c) replicating said cDNA sequence and attached promoter sequence;
(d) placing replicated sequences of step (c) in an in vitro environment comprising an RNA polymerase regulated by said promoter sequences so as to permit transcription of functional RNA transcripts corresponding to said cDNA;
(e) isolating functional RNA transcripts from the materials of (d).

Useful promoters are as described above, and useful RNA polymerases such as those of *E. coli* and phages T3, T7 and SP6 are similarly known to the art, as are in vitro conditions for RNA transcription and suitable vectors not requiring nor providing the high tolerance of this invention.

The vectors utilized for the in vitro transcription processes of this invention need not have a restriction site or part thereof with a cleavage point immediately 5' to the transcription initiation nucleotide. In other words, they need not be constructed using the universal transcription vector of this invention. All that is necessary is that the transcription initiation site corresponds to, or is one base upstream from, the nucleotide corresponding to the extreme 5' nucleotide of the functional RNA.

A functional RNA as used herein means an RNA which is capable of performing the function its corresponding RNA performs in nature, e.g., tRNA, rRNA, snRNA, and preferably viral RNA. The functional RNAs may be modified so as to no longer perform the function intended by nature, for example viral RNA may be made symptomless, tRNA may be mutated, etc.; however, so long as the RNA transcripts are capable of substituting for the corresponding unmodified RNAs, they are considered functional for purposes of this discussion. Functional RNA's also include RNA's capable of translation to produce useful proteins.

This invention also includes the functional, high-tolerance RNA transcripts produced by the above-described processes.

Bacterial strains containing and replicating the above-described vectors are also included within the scope of this invention. Many suitable bacterial strains are known to the art. Preferable strains are *E. coli* K12JM101 and *E. coli* K12JM103.

Appl. Genet. 2:1-10. This vector contains the $P_R$ lambda phage promoter, the cro gene ribosome binding site and a repressor gene for $P_R$. This vector was used as a source of the strong $P_R$ promoter for vector constructions described in the Examples. The BamHI-ClaI DNA fragment containing the promoter is indicated in the figure.

Figure 2:
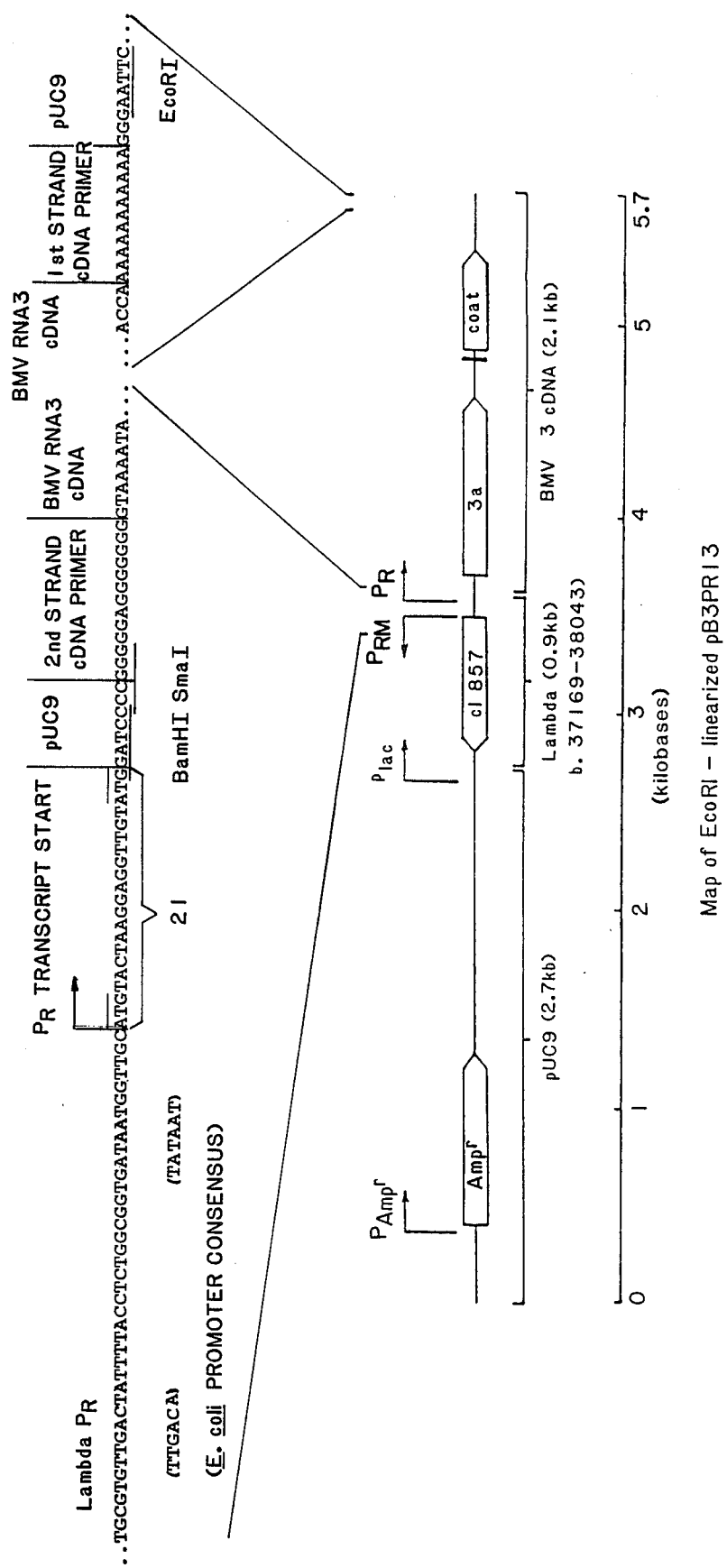

FIG. 2 is a schematic diagram of the vector that resulted from initial fusion of the $P_R$ promoter to the polylinker of pUC9 followed by insertion of the synthetic brome mosaic virus cDNA3 transcript at the SmaI site of the polylinker. As is indicated, in this construct there are 21 nucleotides between the transcription start site of $P_R$ and the 5'-end of the cDNA transcript.

Figure 3:
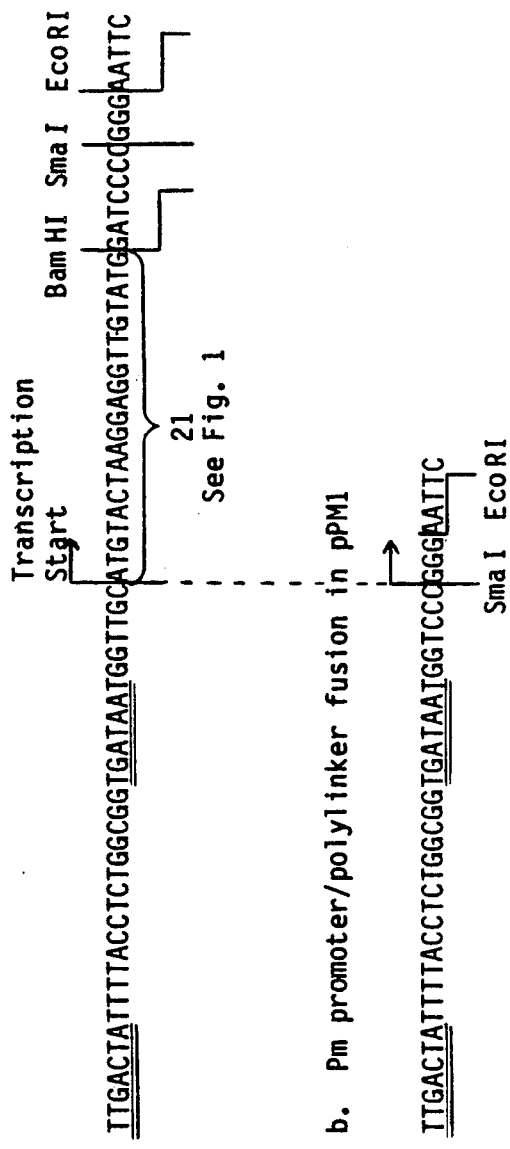

FIG. 3 is a comparison of the DNA sequence in the $P_R$ promoter/transcription start region of the vectors pPR1 and pPM1. The vector pPR1 contains $P_R$ fused to the pUC9 polylinker. The vector pPM1 results from the modification of pPR1 to position a SmaI site the cut site of which coincides with the transcription start site of $P_R$. The vector pPM1 also contains an EcoRI site directly upstream of the SmaI site.

Figure 4:
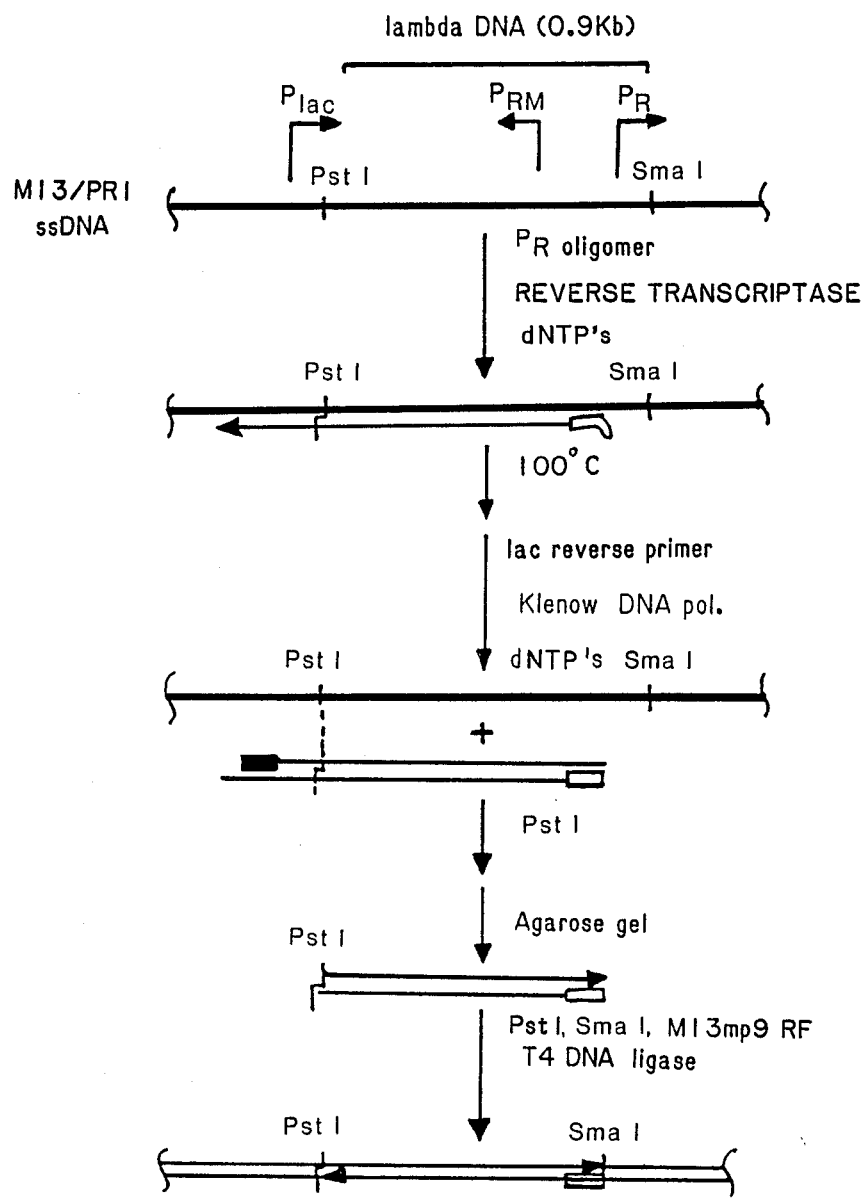

FIG. 4 is a diagram which outlines the procedures employed to insure successful priming of the synthesized mismatched primer used for introduction of the restriction site by oligonucleotide directed mutagenesis. The strategy employed included use of reverse transcriptase and complete denaturation followed by slow renaturation of the template in the presence of high concentration of mismatched primer.

Figure 5:
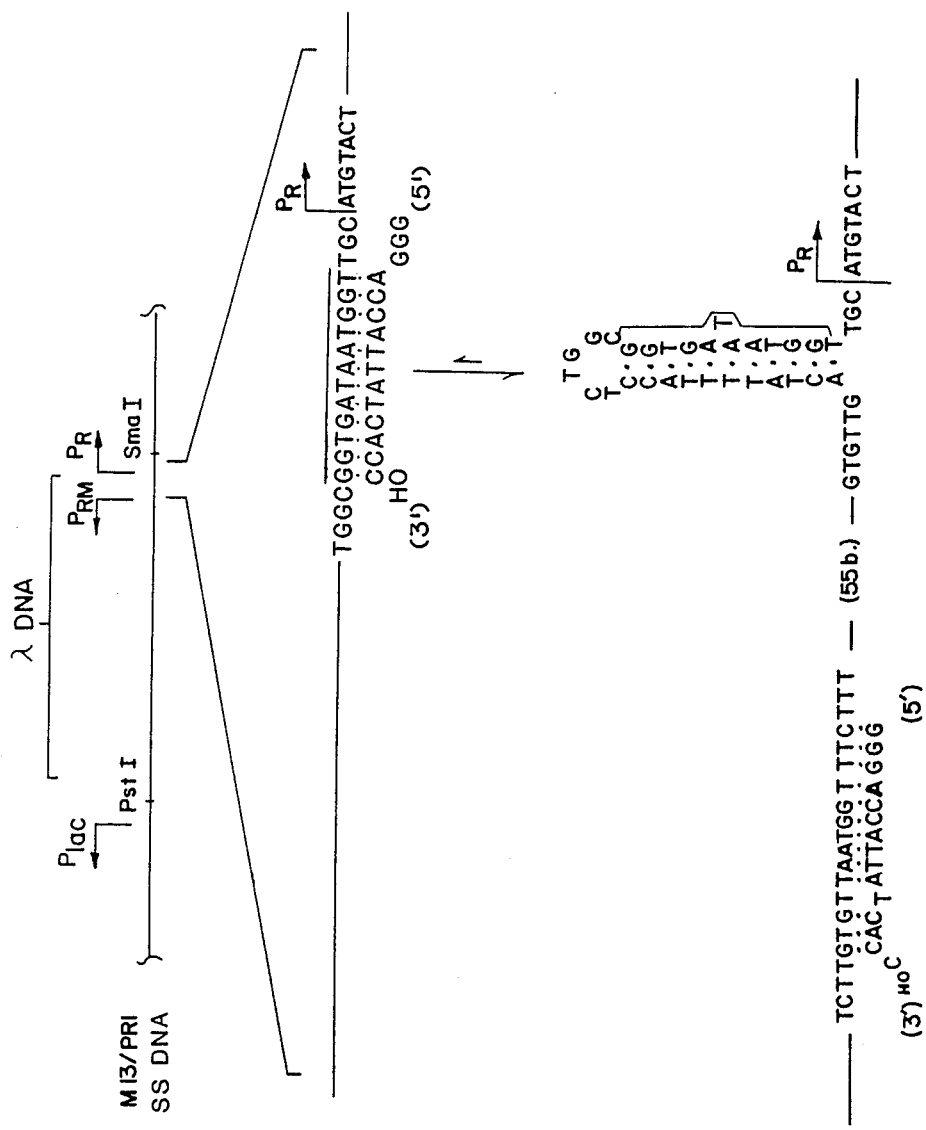

FIG. 5 is a schematic diagram of the promoter/transcription intitiation region in M13/PR1, indicates the non-mutated sequence near the transcription initiation site and indicates how the synthesized mismatched primer should bind in that region. It is believed that initial attempts to obtain priming were unsuccessful because of the presence of a stem and loop structure near the transcription initiation site of M13/PR1. This structure is indicated in the figure.

DETAILED DESCRIPTION OF THE INVENTION

A key feature of the present invention is the construction of recombinant expression vectors with strong promoter elements and restriction endonuclease sites positioned downstream from the promoter so that transcription initiation always occurs at a precise nucleotide. Another critical feature of the present invention is the discovery that, following the conversion of viral RNA molecules to cDNA by the use of reverse transcriptase, these cDNA molecules can be transcribed in vitro into RNA, and that such viral RNA molecules transcribed in vitro from cDNA molecules are infectious, provided that transcription, initiation and transcription termination are essentially at the correct nucleotides.

To be useful in the transmission of foreign genes into plants, DNA fragments are incorporated into suitable positions on the cDNA molecule. For example, using brome mosaic virus which has a tripartite genome (i.e., RNA1, RNA2 and RNA3), it is possible to delete the nucleic acid sequence coding for the coat protein in RNA3 and replace it with the sequence coding for a foreign gene. Such a deletion and replacement is most easily done by use of the cDNA molecule.

This strategy has several attractions: (a) Gene 3a occurs as one of the two open reading frames of RNA3 and it is necessary for this gene to be present for viral RNA replication within plant cells. The requirement for gene 3a function would serve to maintain the engineered component in the virus; (b) The foreign protein would presumably be strongly expressed by the same mechanisms which lead to strong coat protein production in normal infection; (c) The size of the inserted sequences would not be limited by encapsidation constraints; (d) The lack of viral coat protein should limit the escape of engineered virus from deliberately inoculated plants. If both the 3a and coat genes (encoded by RNA3) were required for infection, they could be separated onto two different components, one and coat genes (encoded by RNA3) were required for infection, they could be separated onto two different components, one or both of which could also carry foreign genetic information. Up to 2kb of foreign sequence may be inserted in a single such component without violating packaging constraints.

Many other viruses are useful for the in vitro production of infectious RNA molecules by transcription from cloned cDNA, including various other plant viruses [e.g., tobacco mosaic virus (TMV)], poliovirus, influenza virus, foot and mouth disease virus, and others.

There is yet another benefit to be obtained from the in vitro transcription of viral mRNA molecules from cDNA. It is possible to produce mutations in the viral cDNA molecules that convert a virulent strain to a symptomless strain. Such symptomless strains are used for in vitro synthesis of viral mRNA which is genetically engineered to contain foreign genes. Infection of plants by such symptomless strains of virus can also prevent later superinfection of these plants by virulent strains of virus.

Another use of a recombinant vector carrying a strong promoter and allowing transcription start no more than one nucleotide upstream from the naturally-occurring RNA to which corresponding transcripts are desired is the use of mutated rRNA molecules to combat bacterial infections. rRNA molecules are transcribed from rDNA. Thus, it is possible to mutate the 3' end of the bacterial 16S rRNA molecule in such a way that the rRNA takes its place in the ribosomes but is incapable of mediating translation of mRNA molecules. Multiple transformation of bacteria by a recombinant vector containing such a mutated rRNA severely retards or eliminates bacterial infection. Similarly, mutated tRNA's which are transcribed from tDNA's could be used for the multiple transformation of bacterial populations. Such mutated tRNA's can cause a severe disruption of the bacterial capability to translate mRNA's into needed proteins.

Yet another use of the transfer vectors described herein is the enhancement of translation of a mRNA transcribed from a eukaryotic gene in a transformed bacterium. It is well known in the art that tRNA populations of bacteria occur in different proportions compared to the tRNA populations of eukaryotes and that codon usage is different in the mRNA's of prokaryotes and eukaryotes. Translation of a mRNA transcribed from a eukaryotic gene in a transformed bacterium can be optimized by further transforming a variety of DNA's encoding tRNA's under the control of a promoter into the transformed bacterium.

In order to clone these various DNA molecules from which precisely initiated and terminated ("high resolution") transcripts are required, it is necessary to construct a recombinant plasmid where the DNA to be transcribed is inserted at a precise distance downstream from the regulatory signals of a strong bacterial or viral promoter. Bacteriophage promoters frequently provide strong initiation signals because an infecting virus must redirect the cellular metabolism of a host to its own purposes. It has been shown that lambda $P_R$ promoter initiates transcription many times more frequently than bacterial promoters such as gal or lac (Queen, C. and M. Rosenberg (1981) Cell 25:241-249).

In previous work to increase the production of proteins (Queen, C. (1983) J. Mol. Appl. Genet. 2:1-10), an expression vector was created by placing the $P_R$ promoter and cro gene ribosome binding site on a plasmid, along with a repressor gene for $P_R$ in such a way that the cro ribosome binding site could be easily linked to foreign genes. The effectiveness of this vector was shown by producing two proteins, β-galactosidase and SV-40 small t-antigen, at the level of 5-10% of total E. coli protein. The level of t-antigen achieved ($4 \times 10^5$ molecules/cell) was about 10 times higher than was obtained with the lac system (Thummel, S., Burgess, T. L. and R. Tijian (1981) J. Virol. 37:683-697) or a chemically synthesized ribosome binding site (Jay, G., Khoury, G., Seth, A., and Jay, E. (1981) Proc. Nat. Acad. Sci. U.S.A. 78:5543-5548) and is 20 times higher than the level of interferon obtained using a triple trp promoter (Goeddel, D. V., Shepard, H. M., Yelverton, E., Leung, D. and R. Crea (1980) Nucleic Acids Res. 8:4057-4073).

This expression vector which carried the $P_R$ phage lambda promoter (Queen, C. (1983) J. Mol. Appl. Genet. 2:1-10) was the starting point for creating an entirely novel vector, namely, a vector carrying a strong promoter with a restriction site downstream from the regulatory sequences of the strong promoter precisely at the transcription initiation site. Since the restriction site can be used to insert foreign DNA, this means that transcription initiation of any foreign DNA can be precisely positioned.

In the construction of these transcription initiation vectors, one is not confined to the use of the $P_R$ lambda phage promoter. Any suitable promoter may be used; such a promoter may be strong or weak and subject to regulation by activators and/or repressors. A representative list of such promoters would include (but not be restricted to) the following list: (a) Bacterial promoters such as galP1 (Musso, R. et al. (1977) Proc. Nat. Acad. Sci. U.S.A. 74:106-110) or trp (Bennett, G. N. et al. (1978) J. Mol. Biol. 121:113-137; (b) Other phage promoters such as T3 and T7 promoters, preferably the φ10 T7 promoter (Dunn, J. J. et al. (1983) J. Mol. Biol. 166:477-535; and including the T7 A1 promoter (Siebenlist, U. (1979) Nucleic Acids Res. 6:1895-1907), or those of phage SP6 (Green, M. et al. (1983) Cell 32:681-694); (c) Plasmid and transposon promoters such as pBR322bla (Sutcliffe, J. G. (1979) Proc. Nat. Acad. Sci. U.S.A. 75:3737-3741) and Tn5neo (Rothstein, S. J. et al. (1981) Cell 23:191-199) and promoters created by fusion or mutation such as lacP115 (Johnson, R. C. et al. (1981) Nucleic Acids Res. 9:1873-1883) and IS2 I-II (Hinton, D. M. and R. E. Musso (1982) Nucleic Acids Res. 10:5015-5031). In addition, completely synthetic promoters or promoters recognized by RNA polymerases from biological sources other than bacteria may be used, e.g. fungal, algal, viral, plant or animal; and these promoters may be nuclear or organellar promoters.

Figure 1:
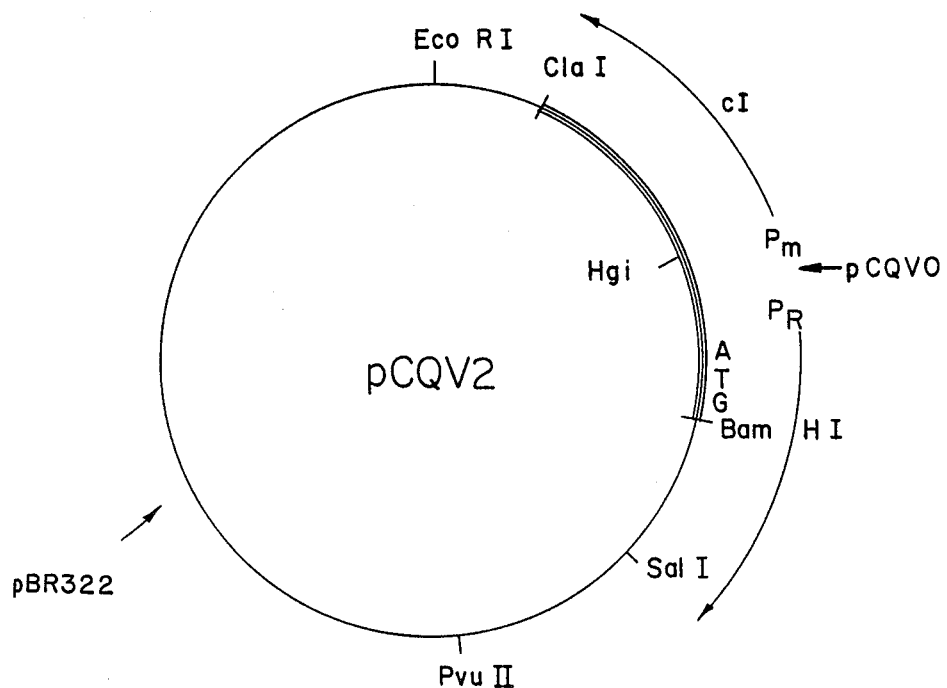
FIG. 1 is a schematic restriction map of the expression vector pCQV2 taken from Queen (1983) J. Mol.

The vectors used in the present invention for the insertion, propagation and manipulation of the BamHI-ClaI DNA fragment from the expression vector pCQV2 (FIG. 1) was M13mp9 (Messing, J. and Vieira, J. (1982) Gene 19:269-276). The M13mp9 in this example was chosen for ease and convenience. The use of this strain is not to be interpreted as excluding the use of other filamentous single stranded phages (e.g., f1 or fd). Other filamentous, single stranded phages could equally well be utilized in these experiments (*The Single Stranded DNA Phages* (1978) Denhardt, D. T., Dressler, D. and D. S. Ray, eds. Cold Springs Harbor Laboratory, New York). M13mp9 was derived from another M13 engineered phage, i.e., M13mp7. The cloning of DNA into the replicative form (RF) of M13 has been facilitated by a series of improvements which produced the M13mp7 cloning vehicle (Gronenborn, B. and J. Messing (1978) Nature, Lond. 272:375-377; Messing, J. (1979) Recombinant DNA Technical Bulletin, NIH Publication No. 79-99, 2, No. 2 43-48; Messing, J., Crea, R. and P. H. Seeburg (1981) Nucleic Acids Res. 9:309-321). A fragment of the *E. coli* lac operon (the promoter and N-terminus of the β-galactosidase gene) was inserted into the M13 genome. This lac promoter-operator insert codes for the first 145 amino acid residues of the β-galactosidase gene. During the infection of certain cell lines (e.g., *E. coli* K12 JM101 and JM103) this information will complement certain deletion mutants of the β-galactosidase gene and restore β-galactosidase activity (α-complementation). These cells show a lac+phenotype and can be identified by a blue colored plaque on a medium containing IPTG and X-gal (Malamy, M. H., Fiandt, M. and Szybalski, W. (1972) Mol. Gen. Genet. 119:207ff). In addition, a small DNA fragment synthesized in vitro and containing an array of restriction cleavage sites [a multiple cloning site (MCS)] was inserted into the structural region of the β-galactosidase gene fragment. In spite of these insertions the M13mp7 DNA is still infective and the modified lac DNA is able to encode the synthesis of a functional β-galactosidase α-peptide (Langley, K. E., Villarejo, M. R., Fowler, A. V., Zamenhof, P. J. and I. Zabin (1975) Proc. Nat. Acad. Sci. U.S.A. 72:1254-1257). This synthesized DNA fragment in M13mp7 contains two sites each for the EcoRI, BamHI, SalI, AccI and HincII restriction enzymes arranges symmetrically with respect to a centrally located PstI site. By chance, either strand of a cloned restriction fragment can become part of the viral (+) strand. This depends on the fragment orientation relative to the M13 genome after ligation. The insertion of a DNA fragment into one of these restriction sites is readily monitored because the insertion results in a non-functional α-peptide and the loss of β-galactosidase activity. Under appropriate conditions, e.g., when strains *E. coli* K12 JM101 or 103 are infected by M13mp7, the functional α-peptide results in blue plaques; a non-functional α-peptide results in colorless plaques (Messing, J. and B. Bronenborn (1978) In Denhardt, D. T., Dressler, D. and D. S. Ray (eds.) The Single Stranded DNA Phages. Cold Spring Harbor Laboratory, Cold Spring Harbor, New York, pp. 449-453). M13mp7 has found wide application in the dideoxy nucleotide sequencing procedure (Sanger, F., Nicklen, S. and A. R. Coulsen (1977) Proc. Nat. Acad. Sci. U.S.A. 74:5463-5467).

A disadvantage of M13mp7 was that the multiple cloning site (MCS) contained two of each kind of restriction endonuclease site thus allowing DNA restriction fragments to be inserted in both orientations. Therefore, two new ssDNA bacteriophage vectors, M13mp8 and M13mp9, were constructed (Messing, J. and Vieira, J. (1982) Gene 19:269-276). The nucleotide sequence of M13mp7, containing the multiple restriction sites, was modified to have only one copy of each restriction site and, in addition, single HindIII, Sma I and XmaI sites. Thus, DNA fragments whose ends correspond to two of these restriction sites can be "forced cloned" by ligation to one of these new M13 cloning vehicles that has also been "cut" with the same pair of restriction enzymes. M13mp8 and M13mp9 have the modified multiple restriction site region arranged in opposite orientations relative to the M13 genome and a given restriction fragment can be directly oriented by forced cloning. The use of both vectors M13mp8 and M13mp9 guarantees that each strand of the cloned fragment will become the (+) strand in one or the other of the clones and thus be extruded as ssDNA in phage particles.

Initially, fusion of the lambda phage $P_R$ promoter to the pUC9 polylinker resulted in 21 nucleotides of lambda sequence and some additional pUC9 nucleotides appearing at the 5' end of the synthetic brome mosaic virus cDNA3 transcript (FIGS. 2 and 3). In order to allow the production of synthetic RNA transcripts (including viral RNA transcripts) with correct 5' termini, a "universal" transcription vector, now designated pPM1, was created. This transcription vector (pPM1) retained most elements of the $P_R$ promoter but the transcription initiation site coincided with the cut side of a unique blunt-end restriction site (the SmaI site in FIG. 3b). The construction of such a transcription vector became possible when examination of a large number of promoter sequences revealed that it might be possible to generate a blunt-end SmaI site at the position of transcription initiation by specific site directed mutagenesis without altering the promoter strength. Transcription of DNA fragments blunt-end ligated into this SmaI site was later demonstrated to begin at the first nucleotide of the inserted fragment. In particular, viral cDNA's were primed by terminally complementary oligonucleotides, blunt-end ligated into this site and transcribed to give the correct 5' ends. Further, the initial form of this vector (FIG. 3b) also provided a unique EcoRI site immediately downstream of the SmaI site where transcription could be runoff-terminated to give product RNA's with no more than seven additional nucleotides at the 3' end.

To construct the pPM1 vector, the lambda cI-$P_{RM}$-$P_R$ cartridge from pCQV2 (FIG. 2) was subcloned into M13mp9. The resulting ssDNA was used as a template for DNA synthesis from a mismatched oligonucleotide designed to fuse the initiation site to the left half of the SmaI recognition sequence. The mismatched oligonucleotide was synthesized by an "in-house" facility. The DNA copied from the mismatch primer was made double stranded, isolated and ligated into M13mp9. After verifying the sequence of the modified $P_R$ promoter (i.e., PM promoter), the new cI-$P_{RM}$-$P_M$ cartridge was subcloned into pUC9 to give the final desired vector pPM1. Several non-trivial technical difficulties were encountered in the use of the mismatch primer. It was found at first that the primer was complementary to a nucleotide sequence which was 96 residues upstream from the $P_R$ promoter and that successful priming was not achieved 3 nucleotides upstream from the $P_R$ promoter initiation site as was expected.

The solution of this unexpected result was finally reached after an exhaustive series of experiments which eliminated other possibilities and showed that the initial cloning protocol failed at the stage of oligomer binding. A comprehensive consideration of possible mechanism of failure to bind oligomer at the desired site and a computer analysis of possible complementary pairing situations culminated in the conclusion that secondary structure in the template was the most likely problem (FIG. 5). This discovery then led to the development of a novel strategy to drive binding to the desired site despite competition from intra-molecular interactions. This novel strategy included use of reverse transcriptase in place of DNA polymerase I Klenow fragment (FIG. 4) and complete denaturation followed by slow renaturation of the template in the presence of a high effective concentration of the mismatched primer. Finally, direct of this newly developed strategy using a wide range of primer concentrations to determine the required levels of primer resulted in effective intitiation of DNA synthesis at the desired position, namely, 3 nucleotides upstream from the $P_R$ promoter initiation site.

The recognition sequence of the SmaI restriction endonuclease is:

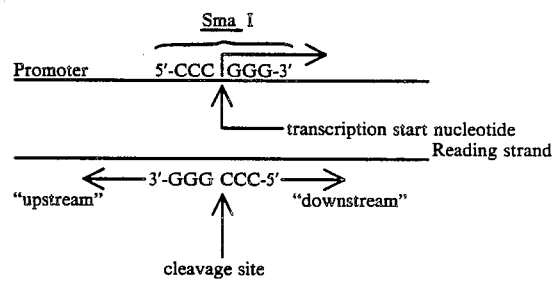

The cleavage site occurs in the center between C and G. The reading strand is 3'-G-G-G-C-C-C-5'. The cleavage site of the SmaI restriction endonuclease is therefore on the 3' side of the transcription intitiation nucleotide with respect to the reading strand. Again, with respect to the reading strand, "upstream" is defined as 5'→3' and "downstream" is defined as 3'→5'.

In general, the critical feature in the construction of universal transcription initiation vectors is the distance between the promoter sequence and the blunt-end cleavage site of a restriction endonuclease. The cleavage site of the restriction endonuclease must be on the 3' side of the nucleotide which is used for transcription initiation on the reading strand such that the cleavage site separates transcribed from untranscribed nucleotides. The term "transcription initiation nucleotide", as used herein, means the first transcribed nucleotide, i.e., the nucleotide corresponding to (or complementary to, depending on the DNA strand) the 5'-terminal ribonucleotide of the RNA transcript.

E. coli RNA polymerase, which recognizes the $P_R$ promoter in pPM1, is capable of transcribing RNAs with a wide variety of 5' end sequences (D. Hawley and W. McClure (1983) Nucleic Acids Res. 11:2237). However, most natural RNAs produced by this enzyme begin with purine. A number of sequences starting with a 5' purine have been linked to the $P_R$ promoter sequences in pPM1 and in all cases tested transcription initiation from $P_R$ began as expected at the initial purine nucleotide of the inserted fragment. (P. Ahlquist and M. Janda (1984) Mol. Cell. Biol. 4:2876).

The next step is to clone exact cDNA copies of the various RNA molecules, i.e., the three genomic RNA's of brome mosaic virus or other viruses (see supra), the 16S RNA of various bacteria and the snRNA's from eukaryotic cells. These steps can be accomplished by synthesizing oligonucleotides complementary to each end of the RNA for use as first and second strand cDNA primers. Once the cDNA's have been synthesized and cloned into the unique restriction site of the universal transcription vector, preferably the SmaI site of the novel pPM1 vector plasmid, it is then possible to synthesize RNA which differ from their authentic natural RNA counterparts only by the addition of a maximum of seven nucleotides to the 3'-end.

Other starting vectors may be used to prepare equivalent universal transcription vectors to those described herein, as will be apparent to those skilled in the art. Similarly, other restriction sites, transcription start sites, primers and the like may be used, so long as the vector constructed provides a cleavage site upstream from and no more than one base away from the transcription initiation site.

The in vitro transcription method provided herein allows for the production of functional RNA transcripts, particularly infectious viral RNA sequences. The transcription plasmids comprising the desired RNA sequences are preferably linearized, preferably with a restriction enzyme immediately downstream from the sequences corresponding to the RNA to be transcribed. The plasmids are placed in an environment containing an RNA polymerase capable of recognizing the promoter sequences. Capping sequences, e.g. m7GppG, are also preferably provided when the product desired is an infectious viral RNA. Other reactants are provided as known to the art, and the reaction mixture is preferably incubated at elevated temperatures, preferably about 37° C., until a number of RNA transcripts from each plasmid have been generated. These transcripts are separated from the reaction mixture and may be used for the purposes described above.

In vitro transcripts of infective RNA's are used in preference to virion RNAs because of their freedom cross-contamination and their greater genetic definition.

Because of variation in the properties of commercial preparations of E. coli polymerase, it is sometimes difficult to obtain consistent production of full-length viral transcripts in good yield. For these and other reasons it is desirable to use transcription vectors with other promoters from which infectious in vitro transcripts can be produced using other types of polymerases, preferably bacteriophage T7 RNA polymerase. This phage polymerase has a much higher activity than the bacterial enzyme and can be easily purified in high yield from overproducing transformed bacterial strains (Davanloo et al. (1984) Proc. Natl. Acad. Sci. USA 81:2035; Tabor and Richardson (1985) Proc. Natl. Acad. Sci. USA 82:1074).

One T7-promoted BMV transcript system which has been used in this invention involves three plasmids, each containing a cDNA insert corresponding to BMV RNA1, 2 or 3, fused in an oligonucleotide-tailored linkage to a T7 promoter to give transcripts with one additional 5' G preceding the viral sequence. This arrangement was selected because it minimizes sequence deviations between the first six bases of the resulting BMV transcripts and a consensus defined by natural T7 promoters (Dunn and Studier (1983) J. Mol. Biol. 166:477). Sequence alterations in this region can adversely affect promoter activity (O. Uhlenbeck, personal communication). The resulting T7/BMV transcripts are produced in much greater yield per plasmid template and have about twice the specific infectivity of previous E. coli/BMV transcripts. Much of the infectivity increase may be due to a greater proportion of full-length product RNA synthesized by the more transcriptionally active and RNAse-free T7 polymerase.

Addition of a single extra 5' G residue has no significant effect on the infectivity of transcripts from cloned BMV cDNA, but addition of 7- or 16-base 5' extensions to RNA3 transcripts dramatically suppresses their biological activity. Moreover, despite the resultant alteration of the promoter consensus sequence, fusion of BMV cDNA directly to the start site of the canonical $\phi$10 promoter of bacteriophage T7 allows efficient in vitro synthesis of infectious BMV transcripts by T7 RNA polymerase, providing a substantial improvement in the ease and reproducibility with which BMV cDNA can be expressed. Uncapped BMV transcripts were found to be infectious to barley protoplasts, although at a lower efficiency than capped transcripts.

Structural features at or near the 5' and 3' ends of many viral RNAs are thought to have important roles in viral replication and expression. Not surprisingly, then, structural alterations at the 5' end of BMV transcripts can significantly modulate infectivity. In particular, the presence of a 5' cap markedly enhances infectivity, while the presence of additional nonviral 5' bases can significantly reduce infectivity.

A variety of independent results demonstrate that presence of a 5' cap structure considerably enhances stability and translational messenger activity of many RNAs in eukaryotic cells (Shih et al. (1976) J. Virol. 19:736; Shimotohno et al. (1977) Proc. Natl. Acad. Sci. USA 74:2734; Contreras et al. (1982) Nucleic Acids Res. 10:6353; Green et al.(1983) Cell 32:681). BMV virion RNA is naturally capped, and in vitro transcripts from either *E. coli* or phage polymerases can be efficiently and conveniently capped by a simple nucleotide substitution method (Contreras et al. (1982) supra; Konarska et al. (1984) Cell 38:731). Such capping considerably enhances infectivity of BMV in vitro transcripts (Ahlquist et al. (1984) Proc. Natl. Acad. Sci. USA 81:7066). In initial whole plant infectivity studies, capped BMV transcripts were readily infectious to whole plants, but uncapped transcripts were not detectably infectious. In protoplasts, where a vastly higher percentage of cells are primarily infectable, uncapped transcripts are detectably infectious, but with an efficiency reduced at least 10-fold compared to capped transcripts. Protoplasts inoculated with all three BMV transcripts, of which two are capped and one uncapped, show that viral RNA replication is highly inhibited by failure to cap either RNA 1 or 2, but is little affected by failure to cap RNA3. That is, in protoplasts coinoculated with capped BMV 1 or 2 transcripts, uncapped BMV3 transcripts can be nearly as effective as capped transcripts in inducing synthesis of progeny RNA3 (R. French, unpublished results). This differential capping sensitivity may result from the need for translation products from both RNA 1 and 2, but not RNA3, to initiate viral RNA replication (Kiberstis et al. (1981) virology 112:804; French et al. (1986) Science 231:1294). Rapid initiation of replication, through enhanced expression of capped BMV 1 and 2 transcripts, overcomes reduced stability of uncapped BMV3 transcripts by producing new and more stable viral RNA copies in first (−) and then (+) strand form. In all the protoplast experiments, a BMV transcript capped with a natural methylated 5' end (M7GppG . . .) was about twice as active as a transcript with an unmethylated cap (GppG . . .).

Although the T7-promoted BMV transcripts described above are highly infectious while bearing an additional nonviral 5' G, larger nonviral 5' extensions can seriously decrease the infectivity of the transcript. The 5' structures of four complete BMV3 in vitro transcripts whose infectivity was examined had either 16, 7, 1 or no additional nonviral bases at the 5' end. When inoculated onto protoplasts with BMV 1 and 2 transcripts with natural 5' ends, each of these transcripts produced progeny RNA3. However, the yield of progeny RNA3 from BMV3 transcripts with 5' extensions of 7 and 16 bases was 20- to 100-fold less than the yield from transcripts with one or no extra 5' bases.

In contrast with the 5' end results, a transcript with 6-7 additional nonviral 3' bases can have nearly the same infectivity as one with a more natural 3' end. We have constructed and tested two different 3' ends on BMV transcripts, both generated by polymerase runoff at a DNA restriction cleavage site. One 3' end is generated by runoff transcription at a PstI site fused directly to the 3' end of BMV cDNA. complete transcription of the template DNA strand at this site would yield a product RNA lacking the terminal A residue of mature BMV virion RNA. However, because of the tRNA-like properties of this end, such an incomplete RNA can be processed to mature form by host cell ATP, CTP: tRNA nucleotidyl transferase (Hoshi et al. (1983) EMBO J. 2:1123). Since this transferase can add all three of the terminal -CCA(3'OH) residues to tRNA, repair would also be expected if transcription terminated one or two residues upstream of the PstI DNA end. Available evidence also suggests that the normal pathway of BMV virion RNA synthesis involves similar non-template-directed addition of the terminal A in consequence of (−) strand initiation at the penultimate residue of the (+) strand template (Miller et al. (1986) J. Mol. Biol. 187:537; Collmer and Kaper (1985) Virology 145:249). Thus the "PstI" 3' transcript end may duplicate a natural BMV replication intermediate, and it is not surprising that transcripts with this 3' end show a high level of infectivity. Another 3' end tested with BMV transcripts is generated by runoff termination at an EcoRI site shortly downstream of the BMV cDNA. Direct sequencing of such "EcoRI" BMV transcripts shows that about half of the transcripts terminate after copying the complete template DNA, while the other half terminate one residue before the end of the DNA (Ahlquist and Janda (1984) Mol. Cell. Biol. 4:2876). This gives rise to a population of transcripts with either six or seven additional 3' bases. The infectivity of these 3'-extended EcoRI transcripts has not been distinguishable from that of the more natural PstI transcripts. Since the additional bases on the EcoRI end must block 3' aminocylation of the transcript, this would indicate that aminocylation of BMV RNA is not required in the initial stages of infection.

The following examples are provided by way of illustration and not by way of limitation.

EXAMPLE 1

Construction and Screening of Phage Recombinants M13/PR1-9

Plasmid pCQV2 (Queen (1983) J. Mol. Appl. Genet. 2:1–10) was cleaved with restriction endonucleases ClaI and BamHI and the fragment containing the phage lambda $cI^{ts}$-$P_{RM}$-$P_R$-ATG sequences was isolated from a low-melting point agarose gel (Sanger et al. (1980) J. Mol. Biol. 143:161–178) and ligated into calf intestinal phosphatased AccI+BamHI cut M13mp9 RF DNA using T4 DNA ligase. This DNA was used to transform competent E. coli JM101 cells and plated. Nine white plaques were selected and screened by the ddATP sequencing technique (Sanger et al. (1982) JMB 162:729–773). The resulting autoradiograph confirmed that eight of the nine phage clones contained the expected phage lambda DNA insert, the remaining clone being a deletion mutant of M13mp9. One of the M13/λ recombinants, designated M13/PR1, was selected for further work.

EXAMPLE 2

Optimum Primer Concentrations for Mismatch Priming on M13mp9/pPR1 ssDNA

The 15-mer mismatched oligonucleotide 5'-OH-d(GGGACCATTATCACC)-3'-OH which will be referred to as either the $P_R$-oligonucleotide or the $P_R$ primer, was synthesized by the phosphite triester method. This $P_R$ primer was designed in such a manner as to allow a precise alteration of the phage lambda $P_R$ promoter. A number of ways were used to test the priming of this $P_R$ primer on $P_R$ DNA. Because of the presence of the complementary stem and loop in the nucleotide sequence of interest (see supra), the following experiments were designed to test whether complete denaturation of the M13mp9/pPR1 DNA template plus vast excesses of the $P_R$-primer could achieve priming at the lambda $P_R$ promoter and whether such primers annealed at this site could be extended by reverse transcriptase without extension of $P_R$ primers bound at the upstream $cI^{ts}$ site. It will be noted (FIG. 5) that when the $P_R$ primer is bound at the upstream $cI^{ts}$ site that it cannot then pair at the extreme 3' terminus. Such a lack of pairing at the extreme 3' terminus should prevent extension by reverse transcriptase which lacks a 3'-exonuclease activity. Therefore, M13PR1 ssDNA was mixed with $P_R$ oligomer at 1, 10, 100, and 1000-fold molar excesses, annealed by the boiling/slow cooling method (Anderson et al. (1980) Nucleic Acids Res. 8:1731ff) and used as a template/primer complex in ddTTP sequencing reactions using reverse transcriptions (Ahlquist et al. (1981) Cell 23:183–189). Autoradiography of the final gel showed that under these conditions DNA synthesis was primed exclusively from the desired site within the $P_R$ promoter sequence. Efficiency of DNA synthesis increased steadily with $P_R$ primer concentration, being at the highest primer:template ratio (1000:1) as efficient as synthesis from a 5-fold excess of the normal M13/lac sequencing primer (Duckworth et al., Nucl. Acids. Res. 9:1691-1706).

EXAMPLE 3

Use of the PR Oligonucleotide to synthesize and Clone an Altered Promoter Sequence A 1000-fold molar excess of $P_R$ oligomer was mixed with approximately 2μg M13/PR1 ssDNA and annealed by the boiling/slow cooling method (Anderson et al. (1980) Nucl. Acids Res. 8:1731ff). The resulting template/primer complexes were extended by reverse transcriptase in the presence of all four dNTPs. The product DNA was isolated by ethanol precipitation and used in a second DNA synthesis reaction primed with an M13 lac "reverse" primer as described by Hong (Bioscience Reports 1:243-252 (1981)). The resulting DNA products were cleaved with PstI, electrophoresed on a low-melting point agarose gel, and the 800-1000 bp fraction, as assayed by the mobility of defined marker DNA fragments, excised and eluted (Sanger et al. (1980), J. Mol. Biol. 143:161-178). This DNA was then mixed with SmaI+PstI cut M13mp9 RF DNA. treated with T4 DNA ligase, and used to transform competent E. coli JM101 cells. After plating, 30 white plaques were selected and screened by the ddATP sequencing method (Sanger et al. (1982) JMB 162:729-773). The pattern obtained for 16 of these recombinants was consistent with the desired construct in which the sequence of the lambda $P_R$ promoter element was linked directly to the vector SmaI site.

Since the purpose of the PM clone constructions was to obtain a particular altered promoter sequence (i.e., a SmaI restriction endonuclease site), two of these recombinants, designated M13 PM86 and M13 PM87, were sequenced by the 2', 3'-dideoxynucleoside triphosphate method (Sanger, F. et al. (1977) Proc. Nat. Acad. Sci. U.S.A. 74:5463-5467). The nucleotide sequence in the vicinity of the altered $P_R$ promoter in both strains was exactly as desired, namely:

```
                                              SmaI
... TGCGTGTTGACTATTTTACCTCTGGCGGTGATAATGGTCCCGGGAATTCACTGGCC ...

PR                                         EcoRI lambda sequence                            M13mp9 sequence
```

The nucleotide sequence changes that have been made at the SmaI site can be seen by a comparison of the above sequence with that of PB3PR13 (FIG. 2). The sequence of M13 PM86 was read for a further 210 bases upstream of the sequence shown above. It was then computer matched to the sequence of pCQV2 (Queen, C. (1983) J. Mol. Appl. Genet. 2:1-10) without any discrepancies. Close visual examination of the autoradiograph revealed no sequence differences between M13 PM86 and M13 PM87.

EXAMPLE 4

Subcloning M13/PM86,87 Inserts into pUC9

For each of the two clones M13 PM86 and M13 PM87, RF DNA was digested with the restriction endonucleases PstI and EcoRI and the EcoRI-PstI fragment containing the desired modified $P_R$ promoter was recovered following electrophoresis in low melting point agarose. The appropriate DNA band (as judged by size) was excised, the DNA extracted as previously described (supra), and ligated to EcoRI+PstI cut pUC9 (Vieira and Messing (1982) Gene 19:259-268). This DNA was used to transform competent E. coli MJ101 cells which were plated on media containing ampicillin, X-gal and IPTG. EcoRI and EcoRI+PstI digests of minilysate DNA samples (Ish-Horowicz and Burke (1981) Nucl. Acids. Res. 9:2989ff) from six white colonies from each ligation mix were examined by agarose gel electrophoresis. In each case the digests confirmed the expected size of the insert fragment and that only one such fragment had been inserted. One of these clones, an M13/PM86 derivative designated pPM1, was selected for further work. Transcripts of pPM1 were obtained by standard methods. Runoff reverse transcription of these transcripts showed that initiation on the $P_R$ promoter occurred precisely at the SmaI site as planned (illustrated below).

```
                        transcript start
                              |
                              v
              TGATAATGGTCCCGGGAATTCACTGGCC
                         ‾‾‾‾‾‾
                          SmaI
```

EXAMPLE 5

Insertion of a Complete cDNA Copy of Brome Mosaic Virus RNA3 (BMV RNA3) Into the SmaI Restriction Endonuclease Cleavage Site of pPM1

The nucleotide sequence of BMV RNA3 is known (Ahlquist, P. et al. (1981) J. Mol. Biol. 153:23-28). Starting from this information, synthetic oligonucleotide primers for the first and second strands of BMV RNA3 cDNA were designed, synthesized and used to prime production of ds cDNA to BMV RNA3 (Fields and Winter (1982) Cell 28:303-313). Full lengths ds cDNA was isolated from an agarose gel (supra) and inserted into the SmaI site of pPM1. Clones in which the cDNA was oriented to give (+) strand transcripts (i.e., transcripts corresponding in polarity to encapsidated viral RNA) were selected after screening by restriction digestion. Plasmid DNA from such selected clones was cut with EcoRI and transcribed in vitro by standard methods. Results obtained using runoff reverse transcription of the transcripts showed that transcription initiation occurred on the first nucleotide downstream from the SmaI cleavage site of the pPM1 transcription vector.

EXAMPLE 6

Synthesis of infectious BMV transcripts with bacteriophage RNA polymerases

Using standard techniques including restriction endonuclease digestion, DNA ligation, synthetic oligonucleotide-directed deletion, bacterial transformation and DNA sequencing (Maniatis et al. (1982) Molecular Cloning, Cold Spring Harbor Laboratory, Cold Spring Harbor, New York; Biggin et al. (1983) Proc. Natl. Acad. Sci. USA 80:3963-3965), fusions were made between bacteriophage T7 and SP6 promoters and each of the BMV cDNA inserts from clones pB1PM18, pB2PM25 and pB3PM1 (Ahlquist and Janda (1984) Mol. Cell. Biol. 4:2876–2882). These plasmids were deposited with the American Type culture Collection, Rockville, Md. on March 7, 1984 as Nos. 40171 and 40169 respectively.

The cDNA insert of a biologically active BMV RNA3 clone was inserted in the transcription vector pGEM1 available from Promega. The resultant plasmid, pB3GE1, allowed SP6 RNA polymerase transcription (Melton et al. (1984) Nucleic Acids Res. 12:7035–7056) of an RNA containing the entire BMV RNA3 sequence plus 6 extra nonviral nucleotides at its 5' end (Table 1). In initial barley protoplast tests, this transcript was around 100 times less infectious than pB3$_{PM}$1 transcripts, showing that additional nonviral 5' nucleotides could reduce BMV transcript infectivity.

RNA3 cDNA was then fused in closer proximity to bacteriophage T7 late promoter $\phi$10 (Dunn and Studier (1983) J. Mol. Biol. 166:477–535) (provided by John Dunn in the form of plasmid pAR2463). The fusions were constructed between the PstI and EcoRI sites of plasmid pUC119. This plasmid is available from Jeffrey Vieira of the Waksman Institute, Rutgers University, and reproducibly described in Vieira and Messing (1987) Meth. Enzymol. 153:3ff. Because the consensus sequence of natural T7 late promoters extends 6 bases into the transcript, and the effects of sequence changes in this region on promoter activity were not known, two different oligonucleotide-directed fusions were made (Table 1). After linearization with EcoRI, plasmids were transcribed in reactions containing 20 ng/$\mu$l DNA, 0.2 $\mu$/$\mu$l T7 RNA polymerase (Promega Biotec), 400 $\mu$M rATP, rCTP, rTTP, 75 $\mu$M rGTP, 500 $\mu$m m7GpppG or GpppG, 40 mM Tris-Cl pH 7.9, 10 mM NaCl, 6mM MgCl$_2$, 10mM DTT, 2mM spermidine and 1 $\mu$/$\mu$l placental ribonuclease inhibitor (Promega Biotec) for 60 min. at 37° C., producing typically 10–20 RNA transcripts per plasmid template. After transcription, RNAse-free DNAse I (Promega Biotec) was added to 1 $\mu$/$\mu$l and incubated 15 min. at 37° C. The reaction was extracted once with 1:1 phenol-chloroform, NaAc added to 0.3M, RNA precipitated with ethanol, ethanol washed, dried and dissolved in a small volume of ddH$_2$0. This produced transcripts with either one extra 5' G residue (pB3TP7) or no extra 5' residues (pB3TP8). The first fusion was chosen to minimize changes in the promoter consensus region, while the second was chosen because of the proven infectivity of correctly-initiated BMV transcripts. A third fusion of RNA3 cDNA to the T7 promoter, including seven extra 5' nucleotides in the transcript (pB3TP5), was obtained as an intermediate in the construction of the two closer fusions (Table 1). Despite the sequence alterations at the transcription start site, all three T7/BMV3 plasmids gave equal yields of around 10–20 copies per plasmid template when transcripts confirmed that initiation occurred at the positions predicted in Table 1. Protoplast infectivity tests with B1$_{PM}$ and B2$_{PM}$ transcripts showed that pB3TP7 and pB3TP8 transcripts had a much higher infectivity than pB3TP5 transcripts. Based on these results, oligonucleotide-directed fusions of the T7 promoter to RNA1 and 2 cDNAs were similarly made with either one G residue (pB1TP1, pB2TP3) or no residues (pB1TP3, pB2TP5) between the promoter initiation site and the cDNA. The same biologically active set of BMV cDNA inserts, designated the M1 set was used in all clones in this study. For convenience, transcripts produced with bacteriophage T7 or SP6 RNA polymerase will be referred to below by the notation Bx$_y$, where x is the BMV component number and y the number of additional nonviral nucleotides present in the transcript (Table 1).

TABLE 1 pB3GE1 (B3$_{16}$) ... CGATTTAGGTGACACTATA*GAATACAAGCTGTCCC<u>GTAAAATACCAACTAATT</u> ...

pB3TP5 (B3$_7$) ... AATTAATACGACTCACTAT*GGGTCCC<u>GTAAAATACCAACTAATT</u> ...

pB3TP7 (B3$_1$) ... AATTAATACGACTCACTAT*G<u>GTAAAATACCAACTAATT</u> ...

pB3TP8 (B3$_0$) ... AATTAATACGACTCACTAT*<u>GTAAAATACCAACTAATT</u> ...

T7 promoter consensus TAATACGACTCACTAT°GGGAGA

DNA sequences at the promoter-cDNA junctions of several BMV RNA4 cDNA clones. The cDNA corresponding to the 5' end of BMV RNA3 (underlined) is linked to an SP6 promoter in pB3GE1 and to a T7 promoter in the other plasmids. Transcription start sites are shown by a bent arrow, and the text designation for each transcript is shown in parentheses. pB3GE1 and pB3TP5 were each constructed by sequential subcloning and rejoining of suitable restriction fragmdnts from pB3PM1. pB3TP7 and pB3TP8 were derived from pB3TP5 by a process involving oligonucleotide-directed mutagenesis of suitable M13 subclones.

EXAMPLE 7

The infectivities of selected BMV transcript combinations were tested in barley seedling inoculations (Table 2). No significant difference in infectivity was visible between T7 transcripts with natural 5' ends (Bx$_0$) and those with an additional 5' G (Bx$_1$) (Experiment 1). In combination with B1$_0$ and B2$_0$, B3$_1$ transcripts appeared to have a small advantage over B3$_0$ transcripts (Experiment 2), but when the standard deviation between replications of the experiment is considered, this difference is not statistically significant (54±18 vs. 44±16). Additional observations of protoplast infectivity confirmed that the activity of the Bx$_0$ transcripts is not less than the Bx$_1$ transcripts. The 5' ends of virion RNA3 from infections with either class of transcript were sequenced and found to be identical to that of wild type virus, showing that the additional 5' G of the B3$_1$ transcript did not persist in its progeny. Notably, Bx$_0$ and Bx$_1$ transcripts had a roughly 20-fold infectivity advantage over Bx$_{PM}$ transcripts. This substantial difference is due to the higher transcript initiation frequency of T7 RNA polymerase, its greater resistance to premature termination under the low rGTP concentrations used for capping and a nonlinear BMV infectivity curve due to the need for co-infection by all three BMV RNAs. In earlier experiments, achieving 30% infectivity with Bx$_{PM}$ transcripts required the product RNA from around 150 ng of each plasmid per plant, compared to the 20 ng used in Table 2 experiments. Moreover, the *E. coli* RNA polymerase used in these earlier experiments produced a much higher transcript yield (2–3 copies/plasmid) than currently available *E. coli*

RNA polymerase lots from several sources (0.3 copies or less). This reduced polymerase performance severely affected experiments even when *E. coli* polymerase transcription reactions were correspondingly scaled up, and was a major incentive for development of the T7 promoter fusions described here.

The infectivity of RNA3 transcripts with various 5' extensions was compared in co-inoculations with B1$_0$ and B2$_0$ transcripts (Table 2). In contrast to the high activity of B3$_0$ and B3$_1$ transcripts, no infections were ever seen when B3$_7$ transcripts were used in the inoculum. A few symptomatic plants were seen in experiments 2 of Table 2 after inoculation with B3$_{16}$ transcripts, but this result could not be reproduced in multiple later attempts, even with increased inoculum concentrations. Infectivity of various BMV transcripts in barley protoplasts paralleled the results of whole plant inoculations. BMV RNA replication induced by Bx$_1$ transcripts was similar to that induced by Bx$_0$ transcripts, and was typically manyfold greater than the biological activity of Bx$_{PM}$ transcripts from a similar amount of plasmid. Transcripts B3$_7$ and B3$_{16}$ failed to induce RNA3 replication detectable by direct protoplast labelling. In these cases low level replication of RNA3, approaching a few percent of that induced by transcripts of pB3TP7 and 8, could be detected by hybridization of electrophoretically separated and blotted protoplast RNA to a suitable RNA3 probe. Uncapped BMV transcripts were previously not detectably infectious to whole plants, and all transcripts in the above experiments were capped by inclusion of m7GpppG in the transcription reaction. However, uncapped transcripts were detectably infectious to protoplasts, although at a lower efficiency than capped transcripts.

All T7 transcripts in this study were made from plasmid templates linearized at an EcoRI site seven bases 3' to the end of the BMV cDNA. In addition, we find that T7 RNA polymerase produces infectious transcripts with similar efficiency from cDNA templates linearized at a PstI site fused to the cDNA 3' end.

TABLE 2

| | Whole Plant Infectivity Tests | | |
|---|---|---|---|
| | Infected plants/ Inoculated plants | | Average percent |
| Experiment 1 | A | B | infected |
| Mock inoculated | 0/21 | 0/22 | 0 |
| BMV virion RNA | 26/45 | 31/57 | 56 |
| B1$_0$, B2$_0$, B3$_0$ | 10/42 | 10/58 | 20 |
| B1$_1$, B2$_1$, B3$_1$ | 5/42 | 16/51 | 23 |
| B1$_{PM}$, B2$_{PM}$, P3$_{PM}$ | 0/46 | 1/60 | 1 |
| Experiment 2 | A | B | |
| Mock inoculated | 0/14 | 0/24 | 0 |
| BMV virion RNA | 18/29 | 33/44 | 70 |
| B1$_0$, B2$_0$, B3$_0$ | 9/29 | 23/43 | 44 |
| B1$_0$, B2$_0$, B3$_1$ | 12/30 | 26/40 | 54 |
| B1$_0$, B2$_0$, B3$_7$ | 0/28 | 0/38 | 0 |
| B1$_0$, B2$_0$, B3$_{16}$ | 1/27 | 4/44 | 7 |

7-day old barley plants were inoculated as indicated with no RNA mock), virion RNA (50 ng/plant), or in vitro transcripts and scored for the presence of mosaic symptoms 7-14 days after inoculation. For each experiment, complete independent replications (A, B) were performed on separate days. Transcripts were produced from EcoRI-linearized plasmids with either T7 or SP6 RNA polymerases (N.E. Biolabs or Promega), except that rGTP concentration was reduced to 75 μM and 500 μM m7GpppG (N.E. Biolabs) was added. Where used, transcripts from approximately 20 ng of each plasmid were applied per plant.

EXAMPLE 8

To determine which portions of RNA3 contribute to its productive replication in infected cells, infectious in vitro transcripts from cloned BMV cDNA were used to generate and analyze systematic deletions in RNA3 cDNA. Suitable deletions, bounded either by specific restriction sites or Bal31 digestion end points, were constructed in plasmid pB3PM1, in which RNA3 sequences are fused to an *E. coli* RNA polymerase promoter or in plasmids pB3TP7 and pB3TP8 (having the T7 promoter). In vitro transcription of such clones produced deleted versions of RNA3 which were tested for their ability to be replicated in barley protoplasts coinoculated with RNA1 and 2 cDNA transcripts. Net viral RNA synthesis in infected cells was assayed after gel electrophoresis by hybridization with an RNA probe complementary to the conserved 3' terminal 200 bases of BMV genomic and subgenomic RNA's. Protoplasts inoculated with only RNA1 and 2 transcripts, or with all three wild type genomic transcripts, served as controls. Such hybridization assays allowed detection of RNA3 at levels several hundred fold lower than that produced during wild type infection, and the extent of RNA1 and RNA2 replication as a convenient internal standard to assess the efficiency of each inoculation and the ability of each protoplast sample to support viral RNA replication. Amplification of each RNA3 variant was quantitated by densitometry of autoradiographs and the results expressed as per cent accumulation relative to wild type RNA3 after normalization for inoculation efficiency as measured by the amount of RNA1 produced in the infection.

Deletions in the 3a gene: Deletions of 100-500 bases were made in either direction from a central ClaI site in the 3a gene and tested for progeny accumulation in protoplasts. Multiple deletions in the 3a gene were tested, showing that the entire gene or any portion thereof can be deleted with little or no effect on RNA3 accumulation. Deletions from the central ClaI site to within 25 bases of the 3a gene 5' end to the exact 3a gene 3' end, or between both extremes all directed progeny RNA accumulation nearly as efficiently as wild type RNA3. RNA3 replication thus has no specific requirement for either the RNA sequences or protein product of the 3a gene. RNA1 and 2 replication is independent of RNA3, and neither RNA3 nor RNA4 synthesis requires coat protein. (French, R., et al. (1986) "Bacterial gene inserted in an engineered RNA virus: Efficient expression in monocotyledonous plant cells," Science 231:1294-1297 and Kiberstis, P. A., et al. (1981) "Viral protein synthesis in barley protoplasts inoculated with native and fractionated brome mosaic virus RNA," Virology 112:804-808.) Taken together, these results indicate that synthesis of the four major species of BMV RNA does not require known RNA3 gene products. Preliminary results from a finer scale deletion mapping of sequences extending into the 5' noncoding region show that RNA3 accumulation is unaffected until deletions enter the noncoding region itself (bases 1-91), with a decline in replicative ability of the mutants as the deletion endpoint moves closer to the 5' end.

Deletions in the coat gene and 3'-noncoding region: Deletion of a major segment of the coat gene, extending from the SalI site at the beginning of the coat gene to the XbaI site near the end of the gene, has only moderate (three-fold) effect on either RNA3 or 4 production during infection. (French, R., et al. (1986), supra.) Additional deletions extending further in both directions were made and tested in barley cells. Three of these have increasing amounts of 3'-noncoding sequence removed, retaining 200, 162 and 100 bases, respectively, of the 3' terminus. Of these, the one with 200 bases retained accumulated to 40 per cent of the wild type level, the one with 162 retained accumulated to levels several hundred-fold lower than wild type RNA3, and the one with 100 bases retained had undetectable progeny. Similar to previously tested deletions within the coat gene, the one with 200 bases retained also generated a small subgenomic RNA with predicted length of only 216 bases. Extending the 5' boundary of coat gene deletions from the SalI site just within the coat gene to the BglII site 20 bases of 5' of the subgenomic mRNA initiation site had two notable and possibly related effects. Presumably because the subgenomic initiation site was removed, no detectable subgenomic RNA was produced. In addition, genomic RNA3 accumulation for BglII-bounded deletions was several-fold above that of the analogous SalI-bounded deletions such as the one with 200 3'-noncoding bases retained.

Deletion of the intercistronic region seriously inhibits RNA3 replication: Although the results above show that some sequences of the RNA3 intercistronic region may be deleted without affecting RNA3 production, any of a variety of deletions into or across the intercistronic region dramatically reduce RNA3 accumulation, by up to several hundred fold. Progressive deletions from either side of the intercistronic region were used to localize the area responsible for this behavior. As deletions extended from 48 to 140 bases into the 5' side of the intercistronic region, RNA3 accumulation was progressively reduced. In each case, the level of RNA4 was also reduced so that the molar ratio of RNA4:-RNA3 remained near the 1:1 ratio of wild type RNA3. A deletion extending from the ClaI site near the center of gene 3a (which extends to about base 1000), to base 1015 replicated at near wild type levels, indicating that the 5' boundary of the active region defined by these assays lies between bases 1015 and 1051. The 3' boundary of required intercistronic sequences identified above does not extend beyond the BglII site near the beginning of the RNA4 gene. This 3' boundary was further mapped using deletions extending from within the coat gene to various endpoints 5' to the BglII site. Repeated experiments revealed small but progressive reductions in RNA3 accumulation until such deletions extend into or beyond the vicinity of the intercistronic AvaI site (base 1147). When this occurs, RNA3 accumulation is again reduced several hundred fold. Consequently, the intercistronic region with maximal effect on RNA3 accumulation does not include the internal oligo(rA) sequence of heterogenous length which occurs immediately 5' to the BglII site.

While these results indicate that a subset of the intercistronic region contributes to RNA3 accumulation, all the intercistronic deletions had at least one end point well inside adjoining coding regions. To confirm that the effect was entirely due to deletion of intercistronic sequences, three additional mutants with smaller deletions were constructed. Two of these had only intercistronic sequences deleted (bases 1013-1142, and bases 1013-1221), and a third (bases 1013-1253) deleted only to the beginning of the coat cistron. Even this small deletion in the coat cistron region reduced the level of RNA3 to nearly the same extent as the larger deletions, confirming that the intercistronic sequences upstream of the oligo(rA) are important for RNA3 accumulation. In addition, a 221 base intercistronic segment encompassing the entire region implicated above (bases 1004-1225) was inverted in the strongly replicating variant containing bases 604-1225. Similar to deletion of the entire intercistronic region, accumulation of not only (+) but also (−) strand RNA was severely inhibited with the reversed variant, showing that this intercistronic segment functions only in appropriate orientation relative to other elements of BMV RNA3.

Simultaneous deletions in the 3a and coat genes: As noted above, nearly complete or complete deletion of either the 3a or coat genes had only small effects on production of RNA's 3 or 4. However, when major deletions in both coding regions occurred simultaneously in the same molecule, (bases 101-1003 and 1258-1760; bases 117-601 and 1258-1917; and bases 117-1003 and 1258-1917), RNA3 levels were again reduced over one hundred fold. Among tested mutants with deletions in both genes, only one with deletion of bases 604-1003 and 1258-1917 which retained the 5' half of the 3a gene and has the least total amount of sequence removed, accumulated to readily visible amounts, but was still depressed compared to wild type RNA3. A possible, but unlikely explanation for these results was that expression of either the coat protein or the N-terminal domain of the 3a protein, though not both, was required for efficient RNA3 amplification. To test this, an RNA3 derivative with deletions of bases 100-110 and 1253-1254 with frameshift mutations just within the 5' boundaries of both the 3a and coat cistrons was constructed. This mutant both replicated and generated subgenomic RNA at levels comparable to wild type RNA3, confirming that neither RNA3 nor RNA4 synthesis depends on the known RNA3 gene products.

The mutant with deletions from bases 101-1003 and 1258-1760 was further modified by inserting the bacterial chloramphenicol acetyltransferase (CAT) gene sequence in place of the deleted coat gene. Despite its heterologous nature, this insertion dramatically improved RNA3 accumulation, giving 17 per cent of the wild type RNA3 level. This equals the accumulation of an RNA3 derivative with an intact 3a gene and the same CAT insertion, suggesting that the remaining reduction of accumulation relative to wild type RNA3 is due to the presence of CAT sequences rather than the absence of BMV sequences.

Effects of deletions and rearrangements on accumulation of RNA3 (−) strands: Normal BMV infections induce highly asymmetric production of (+) and (−) viral RNA strands, with wild type RNA3 yielding about a 100-fold excess of (+) strands after 20 hour infection of barley protoplasts. The relative levels of (−) and (+) strand genomic RNA accumulation were also tested for a number of deletion mutants discussed above. These levels were tested by probing parallel blots of the same gel-electrophoresed RNA samples with suitable (+) and (−) strand probes. Reactivity and specific activity of the two different probes was normalized by comparison of the hybridization signals of BMV RNA standards of known concentration. For all variants tested, the ratio of (+) to (−) strand RNA3 was similar to that of wild type BMV, indicating no significant differential in overall effects on RNA3 (+) or (−) strand accumulation.

The foregoing examples are illustrative of this invention, and as will be understood by those skilled in the art, many equivalent constructions and organisms may be prepared by methods analogous, similar or otherwise equivalent to those, specifically discussed herein. For example, because transcripts having one extra 5' base have been found to be functionally equivalent to those having no extra 5' bases, vectors functionally equivalent to pPM1 and other similar vectors allowing insertion of a nucleotide sequence to be transcribed at a restriction site whose cleavage site is immediately upstream from the transcription initiation nucleotide are those in which the transcription initiation nucleotide is immediately upstream of the cleavage site, so that there is one additional base on the 5' end of the transcribed sequence. Similarly, vectors equivalent to pPM1 with nucleotide sequences inserted therein which produce transcripts with no additional 5' bases are similar vectors having nucleotide sequences inserted therein which produce transcripts having one additional 5' base.

Plasmid pPM1 was deposited Mar. 7, 1985, with the American Type Culture Collection, 12301 Parklawn Drive, Rockville, Md., as No. 40172.

What is claimed is:

1. A recombinant DNA vector comprising
   (a) a replication origin, a selectable marker and
   (b) a nucleotide sequence comprising a promoter, a transcription initiation site of which has been modified by introducing a restriction endonuclease recognition sequence such that a cleavage site of said restriction endonuclease recognition sequence coincides with said transcription initiation site of said promoter and wherein said promoter does not naturally contain a restriction endonuclease sequence a cleavage site of which coincides with a transcription initiation site of said promoter.

2. A bacterial strain containing and replicating therein the vector of claim 1.

3. A bacterial strain as recited in claim 2 wherein said strain is selected from the group consisting of *Escherichia coli* K12 JM101 and *Escherichia coli* K12 JM103.

4. A vector as recited in claim 1 wherein said replication origin and selectable marker are selected from the group consisting of the replication origins and selectable markers of pUC9 and M13mp9.

5. A vector as recited in claim 1 wherein said promoter is the $P_R$ lambda phage promoter.

6. A vector as recited in claim 1 wherein said restriction endonuclease recognition sequence is a blunt-ended restriction endonuclease sequence.

7. A vector as recited in claim 1 wherein said restriction endonuclease recognition sequence is a SmaI restriction endonuclease sequence.

8. A vector as recited in claim 1 also comprising a second endonuclease recognition sequence positioned immediately 3' to said endonuclease recognition sequence.

9. A vector as recited in claim 1 wherein said promoter is selected from the group consisting of promoters of PR lambda phage, T3, T7, SP6 and synthetic promoters.

10. A vector as recited in claim 1 wherein said promoter is a synthetic promoter.

11. A vector as recited in claim 1 wherein said promoter comprises T7 promoter sequences.

12. A vector as recited in claim 1 wherein said promoter comprises SP6 promoter sequences.

13. A vector as recited in claim 1 wherein said promoter comprises T3 promoter sequences.

14. Recombinant plasmid vector pPM1, ATCC Deposit No. 40172.

15. A recombinant DNA vector comprising
    (a) a replication origin, and a selectable marker,
    (b) a nucleotide sequence comprising a promoter, a transcription initiation site of which has been modified by introducing a restriction endonuclease recognition sequence such that a cleavage site of said restriction endonuclease recognition sequence coincides with said transcription initiation site of said promoter and wherein said promoter does not naturally contain a restriction endonuclease sequence a cleavage site of which coincides with a transcription initiation site of said promoter, and
    (c) a fragment of DNA inserted at said cleavage site such that the first nucleotide that will be transcribed is the first nucleotide at the 5' end of said inserted fragment of DNA.

16. A vector as recited in claim 15 wherein said fragment of DNA comprises sequences coding for viral RNA.

17. A recombinant vector as recited in claim 15 wherein said fragment of DNA comprises sequences coding for mutated viral RNA.

18. A recombinant vector as recited in claim 15 wherein said fragment of DNA codes for an RNA selected from the group consisting of rRNA, tRNA and snRNA.

19. A recombinant vector as recited in claim 15 wherein said fragment of DNA codes for a mutated snRNA.

20. A recombinant vector as recited in claim 15 wherein said fragment of DNA comprises sequences corresponding to BMV viral RNA.

21. A recombinant DNA vector as recited in claim 15 wherein said fragment of DNA is a cDNA molecule derived by reverse transcription from a viral RNA molecule and wherein said fragment is inserted in such a way that the end of the cDNA molecule that corresponds to the 5' end of said viral RNA molecule is positioned adjacent to the 3' end of said promoter.

22. A recombinant DNA vector as recited in claim 15 wherein said restriction endonuclease recognition sequence is a blunt-end restriction endonuclease recognition sequence.

23. A recombinant DNA vector as recited in claim 15 wherein said promoter is a bacteriophage promoter.

24. A recombinant DNA vector as recited in claim 15 wherein said fragment of DNA is inserted at the SmaI site of the recombinant vector pPM1.

* * * * *

UNITED STATES PATENT AND TRADEMARK OFFICE
CERTIFICATE OF CORRECTION

PATENT NO. : 4,885,248

DATED : December 5, 1989

INVENTOR(S) : Ahlquist, Paul G.

It is certified that error appears in the above-identified patent and that said Letters Patent is hereby corrected as shown below:

At column 2, line 39, please rewrite "endonuclease" as --endonucleases--. At column 4, line 57, please rewrite "rRNa" as --rRNA--. At column 7, line 20, after "site" please add --,--. At column 7, line 32, please rewrite "FIG. 5 is" as -- FIG. 5,--. At column 8, lines 13-16, please delete "and coat genes (encoded by RNA3) were required for infection, they could be separated onto two different components, one". At column 9, lines 18-19, please rewrite "E. coli" as --E. coli--. At column 9, line 49, please rewrite "121:113-137;" as --121:113-137);--. At column 9, line 52, please rewrite "166:477-535;" as --166:477-535);--. At column 10, line 58, please rewrite "The Single Stranded DNA Phages" as --The Single Stranded DNA Phages--. At column 13, line 42, please rewrite "RNAs" as --RNA's--. At column 14, line 35, please rewrite "RNAs" as --RNA's--. At column 17, line 21, please rewrite "DNA. treated" as --DNA, treated--. At column 19, line 6, please rewrite "40171 and 40169" as --40171, 40170 and 40169--. At Table 1, bridging columns 19 and 20, second to last line of description, please rewrite "fragmdnts" as --fragments--. At column 19, line 47, please rewrite "µ/µ1" as --U/µ1--. At column 19, line 48, please rewrite "µm" as --µM--. At column 19, line 51, please rewrite "µ/µ1" as --U/µ1--. At column 19, line 55, please rewrite "µ/µ1" as --U/µ1--. At column 21, Table 2, line 58, please rewrite "RNA mock)" as --RNA (mock)--. At column 21, Table 2, line 59, please rewrite

UNITED STATES PATENT AND TRADEMARK OFFICE
CERTIFICATE OF CORRECTION

PATENT NO. : 4,885,248

DATED : December 5, 1989

INVENTOR(S) : Ahlquist, Paul G.

It is certified that error appears in the above-identified patent and that said Letters Patent is hereby corrected as shown below:

"in vitro" as --*in vitro*--.

Signed and Sealed this

Seventh Day of January, 1992

Attest:

HARRY F. MANBECK, JR.

*Attesting Officer*     *Commissioner of Patents and Trademarks*